(12) United States Patent
Stevenson

(10) Patent No.: US 7,199,995 B2
(45) Date of Patent: *Apr. 3, 2007

(54) FEEDTHROUGH FILTER CAPACITOR ASSEMBLY WITH INTERNALLY GROUNDED HERMETIC INSULATOR

(75) Inventor: Robert A. Stevenson, Canyon Country, CA (US)

(73) Assignee: Greatbatch-Sierra, Inc., Clarence, NY (US)

( * ) Notice: Subject to any disclaimer, the term of this patent is extended or adjusted under 35 U.S.C. 154(b) by 33 days.

This patent is subject to a terminal disclaimer.

(21) Appl. No.: 11/386,161

(22) Filed: Mar. 21, 2006

(65) Prior Publication Data

US 2007/0035910 A1    Feb. 15, 2007

Related U.S. Application Data

(63) Continuation of application No. 11/161,730, filed on Aug. 15, 2005, now Pat. No. 7,035,076.

(51) Int. Cl.
*H01G 4/35* (2006.01)
*H01G 4/236* (2006.01)
*H01G 4/228* (2006.01)

(52) U.S. Cl. .................. 361/302; 361/307; 361/306.2; 607/5

(58) Field of Classification Search ............... 361/302, 361/306.1, 306.2, 306.3, 308.1, 308.2, 308.3, 361/309–311, 301.2; 607/5; 333/182–185
See application file for complete search history.

(56) References Cited

U.S. PATENT DOCUMENTS

| 3,920,888 | A | * | 11/1975 | Barr ..................... 174/152 GM |
| 4,152,540 | A | * | 5/1979 | Duncan et al. ...... 174/152 GM |
| 4,421,947 | A | * | 12/1983 | Kyle .................... 174/152 GM |
| 4,424,551 | A | * | 1/1984 | Stevenson et al. .......... 361/302 |
| 5,333,095 | A | * | 7/1994 | Stevenson et al. .......... 361/302 |
| 5,905,627 | A | * | 5/1999 | Brendel et al. ............. 361/302 |
| 6,529,103 | B1 | * | 3/2003 | Brendel et al. ............. 333/182 |
| 6,768,629 | B1 | * | 7/2004 | Allen et al. ................. 361/302 |
| 7,035,076 | B1 | * | 4/2006 | Stevenson ................... 361/302 |
| 2004/0257747 | A1 | * | 12/2004 | Stevenson et al. .......... 361/302 |
| 2005/0201039 | A1 | * | 9/2005 | Stevenson et al. .......... 361/302 |

* cited by examiner

*Primary Examiner*—Eric W. Thomas
(74) *Attorney, Agent, or Firm*—Kelly Lowry & Kelley LLP

(57) ABSTRACT

A feedthrough filter capacitor assembly includes a conductive terminal pin which extends through a first passageway of a capacitor in conductive relation with a first set of electrode plates, and through a conductive ground plane and an insulator in non-conductive relation. The insulator includes ground plates conductively coupled to the ferrule. A second set of electrode plates of the capacitor are conductively coupled to the insulator ground plates, such as by a ground pin extending through the capacitor in relation with the second set of electrode plates, and at least partially extending through a second passageway of the insulator in conductive relation with the ground plates. In this manner, the exterior electrical/mechanical connection between the capacitor and ground plane or other ground member is eliminated.

38 Claims, 9 Drawing Sheets

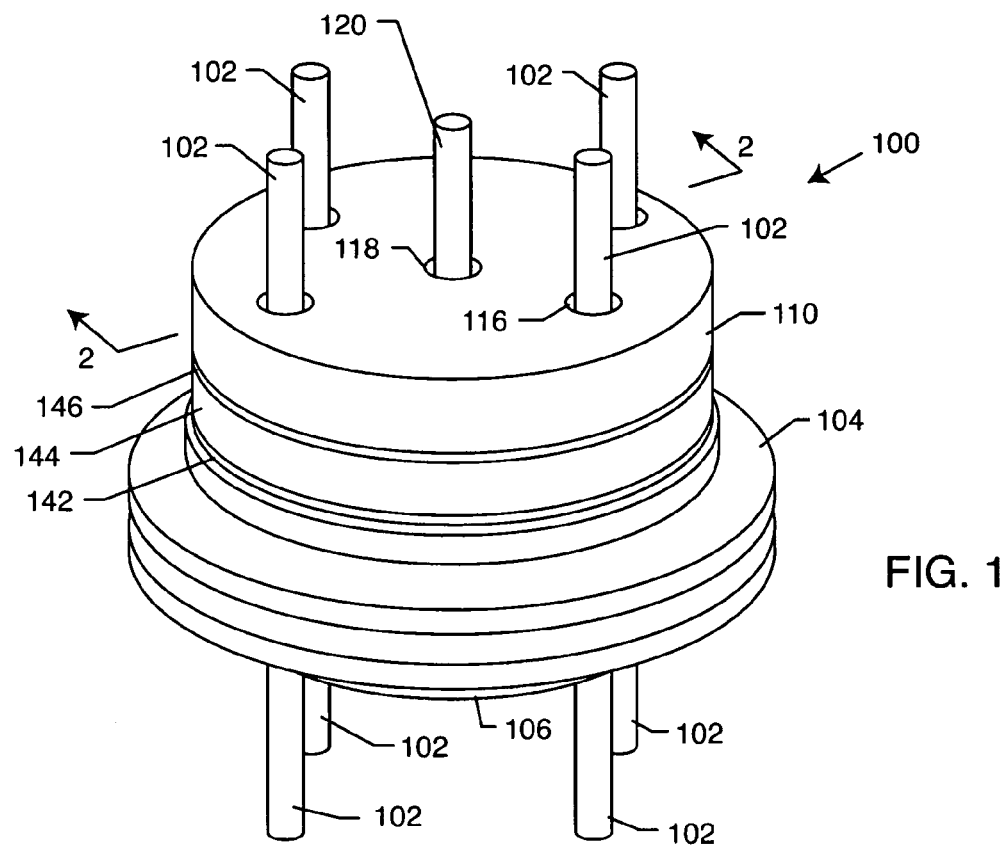
FIG. 1
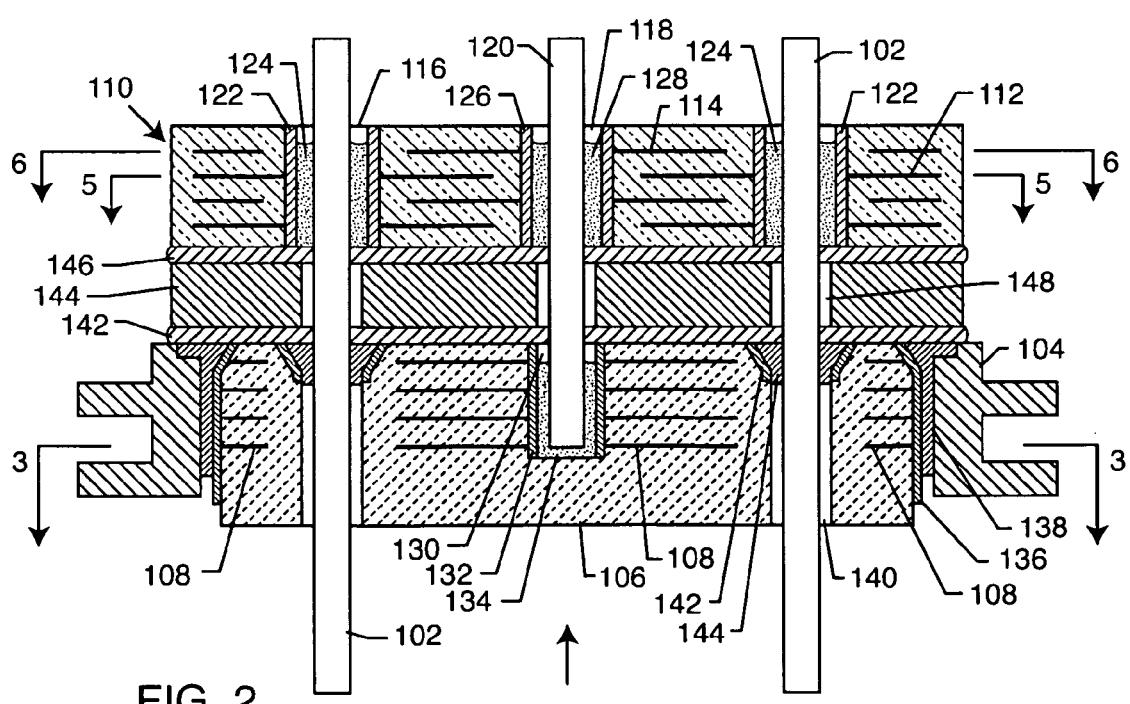
FIG. 2           BODY FLUID SIDE

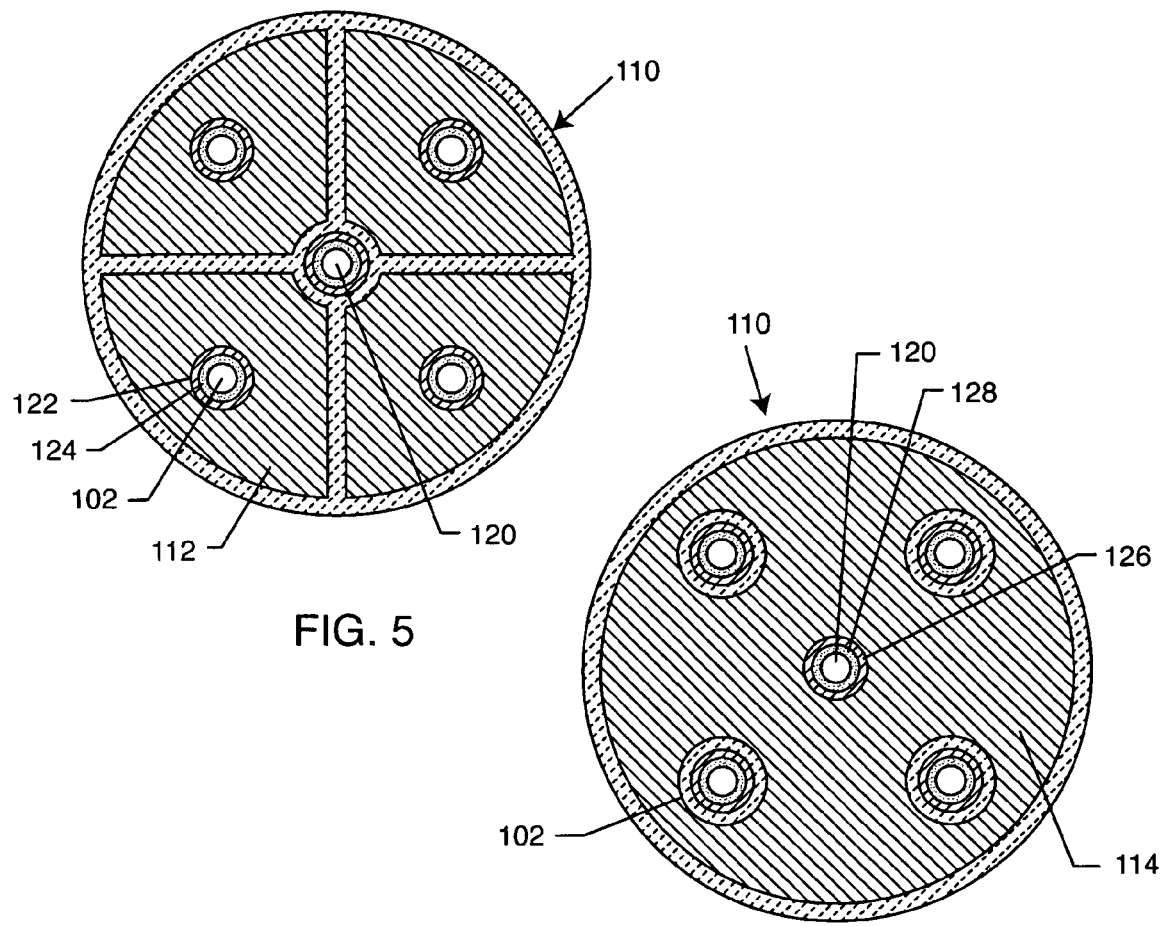
FIG. 5
FIG. 6
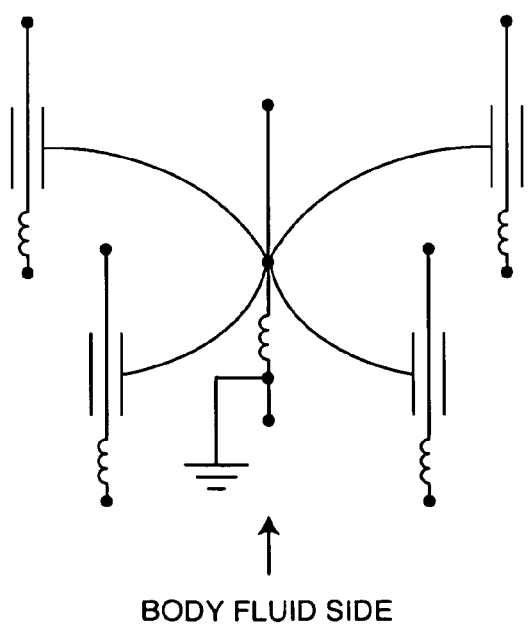
FIG. 7
BODY FLUID SIDE

FEEDTHROUGH FILTER CAPACITOR ASSEMBLY WITH INTERNALLY GROUNDED HERMETIC INSULATOR

This is a continuation of U.S. Ser. No. 11/161,730 filed Aug. 15, 2005, now U.S. Pat. No. 7,035,076.

BACKGROUND OF THE INVENTION

The present invention relates generally to improved feedthrough terminal pin sub-assemblies and related methods of construction, particularly of the type used in active implantable medical devices, to decouple and shield undesirable electromagnetic interference (EMI) signals from the device. More particularly, the present invention relates to a reduced cost and reduced mechanical stress hermetic feedthrough terminal pin and ceramic feedthrough capacitor assembly which does not require an outer electrical connection between the one or more capacitors and a ground plane which is typically found in the form of a ferrule or device housing ground. It is adapted particularly for use in connecting one or more lead wires or conductive terminal pins through a hermetically sealed housing to internal electronic components of the medical device while decoupling EMI against entry into the sealed housing. The present invention is specifically designed for use in active implantable medical devices, such as cardiac pacemakers, implantable defribillators, hearing implants, neuro-stimulators, drug pumps, bone growth stimulators, and the like.

Feedthrough terminal pin assemblies are generally well known in the art for connecting electrical signals through the housing or case of an electronic instrument. For example, in implantable medical devices such as cardiac pacemakers, defibrillators or the like, the terminal pin assembly comprises one or more conductive terminal pins supported by an insulator structure for feedthrough passage from the exterior to the interior of the medical device. Many different insulator structures and related mounting methods are known in the art for use in medical devices wherein the insulator structure also provides a hermetic seal to prevent entry of body fluids into the housing of the medical device. Said hermetic insulators for medical implant applications are typically constructed of alumina ceramic or glass wherein the terminal pins and ferrule are of suitable biocompatible material such as platinum, platinum-iridium, niobium, tantalum or titanium, respectively. However, the feedthrough terminal pins are typically connected to one or more exterior lead wires, for example, the leads which connect a cardiac pacemaker to the ventricle chamber of the heart, can also effectively act as an antenna and thus tend to collect stray EMI signals for transmission into the interior of the medical device. In many prior art devices, the hermetic terminal pin assembly has been combined directly with a ceramic feedthrough filter capacitor to decouple interference signals to the housing of the medical device.

In a typical unipolar construction, as described in U.S. Pat. No. 5,333,095 (the contents of which are incorporated herein), a coaxial ceramic feedthrough filter capacitor used in a feedthrough assembly to suppress and decouple undesired interference or noise transmission along a terminal pin comprises a so-called discoidal capacitor having two sets of electrode plates embedded in spaced relation within an insulative dielectric substrate or base, formed typically as a ceramic monolithic structure. One set of the electrode plates is electrically connected at an inner diameter cylindrical surface of the discoidal capacitor structure to the conductive terminal pin utilized to pass the desired electrical signal or signals. The other or second set of electrode plates is coupled at an outer diameter surface of the discoidal capacitor to a cylindrical ferrule of conductive material, wherein the ferrule is electrically connected in turn to the conductive housing of the electronic device. The number and dielectric thickness spacing of the electrode plate sets varies in accordance with the capacitance value and the voltage rating of the discoidal capacitor. In operation, the discoidal capacitor permits passage of relatively low frequency biological electrical signals along the terminal pin, while shielding and decoupling/attenuating undesired interference signals of typically high frequency to the conductive housing.

Feedthrough capacitors of this general type are available in unipolar (one), bipolar (two), tripolar (three), quadpolar (four), pentapolar (five), hexpolar (six) and additional lead configurations. The feedthrough capacitors of this general type are commonly employed in implantable cardiac pacemakers, defibrillators, and the like, wherein the pacemaker housing is constructed from a biocompatible metal, such as titanium alloy, which is electrically coupled to the second electrode plate set of the feedthrough filter capacitor. As a result, the filter capacitor and terminal pin assembly prevents entrance of interference signals to the interior of the pacemaker housing, wherein such interference signals could otherwise adversely affect the desired cardiac pacing or defibrillation function.

In the past, feedthrough filter capacitors for cardiac pacemakers and the like have typically been constructed by preassembly of the discoidal capacitor within a cylindrical or rectangular terminal pin subassembly which includes the conductive pin and ferrule. More specifically, the terminal pin subassembly is prefabricated to include one or more conductive terminal pins supported within the conductive ferrule by means of a hermetically sealed insulator ring or bead. See, for example, the subassemblies disclosed in U.S. Pat. Nos. 3,920,888; 4,152,540; 4,421,947; and 4,424,551. An improved design which has substantially improved the volumetric efficiency is based upon surface mounting of a ceramic feedthrough capacitor planar array structure to one outer surface of a hermetic terminal with similar connection to the conductive pins (see the subassemblies disclosed in U.S. Pat. No. 5,333,095). In all of the prior art described above, the outer feedthrough capacitor electrode plate sets are coupled in parallel together by a metallized layer which is either fired, sputtered or plated onto the ceramic capacitor. This metallized band, in turn, is coupled to the ferrule by conductive adhesive, soldering, brazing, or the like.

Although feedthrough filter capacitor assemblies of the type described above have performed in a generally satisfactory manner, the manufacture and installation of such filter capacitor assemblies has been relatively time consuming and therefore costly. For example, installation of the discoidal capacitor into the small annular space described by U.S. Pat. No. 4,424,551 between the terminal pin and ferrule can be a difficult and complex multi-step procedure to ensure formation of reliable, high quality electrical connections. The method taught by U.S. Pat. No. 4,424,551 (the contents of which are incorporated herein), teaches the injection of fluidic thermosetting conductive particles into first and second annular cavities (usually by centrifuge operations). As a consequence, this method also requires insulation of the interface between the capacitor structure and insulator, curing of the various thermosetting materials, and subsequent cleaning operations to remove excess conductive material. While the method taught by U.S. Pat. No. 5,333,095 is far simpler, a connection from the capacitor outside diameter and the conductive ferrule is still required.

A significant advance in the state of the art is described by internally grounded feedthrough capacitors as described in U.S. Pat. Nos. 5,905,627 and 6,529,103. These patents describe a methodology wherein it is not necessary to form a direct electrical connection between the outside diameter metallization of the feedthrough capacitor and the ferrule of the hermetic terminal of the implantable medical device. The internal ground technology teaches grounding of the second set of electrode pins through one or more grounded terminal pins. This has a significant advantage in that the elimination of the electrical and mechanical connection from the capacitor outside diameter or perimeter acts to significantly reduce the thermal and mechanical stress that is transmitted to the rather fragile feedthrough capacitor during the installation of the hermetic terminal pin assembly into the housing of the active implantable medical device by laser welding or the like. A significant number of EMI filtered hermetic terminals used in cardiac pacemakers and implantable defibrillators are manufactured using an internally grounded feedthrough capacitor. This has become a very popular and cost effective way of manufacturing such terminals. However, a significant cost driver is the need to provide one or more grounded pins for coupling to the second set of capacitor electrode plates. The present invention describes a novel method of providing internally grounded electrode plates within the hermetic terminal insulator itself. As will be further described herein, such internal ground plates within the insulator can be used to conveniently ground one or more terminal pins to couple to the second electrode plate set of the internally grounded capacitor.

A high integrity hermetic seal for medical implant applications is very critical to prevent the ingress of body fluids into the implanted device (e.g. pacemaker). Even a small leak rate of such body fluid penetration can, over a period of many years, cause moisture to build up and damage sensitive internal electronic components. This can cause catastrophic failure of the implanted device. The hermetic seal for medical implant applications is typically constructed of highly stable alumina ceramic or glass materials with very low bulk permeability.

Withstanding the high temperature and thermal stresses associated with the welding of a hermetically sealed terminal with a premounted ceramic feedthrough capacitor is very difficult to achieve with the prior art designs. The electrical/mechanical connection to the outside perimeter or outside diameter of the feedthrough capacitor has a very high thermal conductivity as compared to air. The hermetic bonding operation typically employed in the medical implant industry to install the filtered hermetic terminal into the implantable device housing generally involves a laser welding operation in very close proximity to this electrical/mechanical connection area. Accordingly, in the prior art, the ceramic feedthrough capacitor is subjected to a dramatic temperature rise. This temperature rise produces mechanical stress in the capacitor due to the mismatch in thermal coefficients of expansion of the surrounding materials. Many of these prior art devices employ a soldered connection to the outside perimeter or outside diameter of the feedthrough capacitor. Excessive installation soldering heat has been known to damage such devices.

The novel internally grounded feedthrough capacitors that are described by U.S. Pat. Nos. 5,905,627 and 6,529,103 solve these issues. By elimination of the outside diameter or outside perimeter electrical/mechanical connection area, the thermal and mechanical stresses are greatly reduced. That is, during laser welding of the titanium flange into the housing of the implantable medical device, said titanium flange will tend to expand and contract greatly. This transmits stresses to the rather sensitive monolithic ceramic feedthrough capacitor. Accordingly, elimination of said mechanical and electrical connection is a highly desirable feature. The present invention describes a very novel and convenient way of making connection to the second set of electrode plates without creating additional mechanical stresses.

A major market force within the medical implantable device industry has been to reduce the cost of the implanted device (e.g. pacemaker or implantable cardioverter defibrillator). Medical insurance carriers, government healthcare programs (e.g. Medicare) and health maintenance organizations (HMOs) are placing additional competitive pressures on the manufacturers of such devices.

Accordingly, there is a need for a novel feedthrough filter capacitor assembly that addresses the drawbacks noted above in connection with the prior art. In particular, a novel capacitor assembly is needed that is subjected to far less temperature rise during the manufacture thereof by eliminating an outside perimeter or outside diameter electrical/mechanical connection. Such a design would allow the use of much lower temperature materials (such as standard solder) to achieve the capacitor inside diameter lead connections. Moreover, such an improvement would make the assembly relatively immune to the aforementioned stressful installation techniques. A novel filter capacitor design is needed which is of simplified construction, utilizing a straightforward and uncomplicated feedthrough terminal pin subassembly that can result in manufacturing cost reductions. Of course the new design must be capable of effectively filtering out undesirable electromagnetic interference (EMI) signals from the target device. The present invention fulfills these needs and provides other related advantages.

SUMMARY OF THE INVENTION

The present invention resides in an improved internally grounded feedthrough filter capacitor assembly, wherein the capacitor assembly is subjected to far less temperature rise during the manufacture thereof by eliminating the outside perimeter or outer surface electrical/mechanical connection. The design of the present invention is capable of effectively filtering out undesirable EMI signals from the target device, while eliminating stressful installation techniques and resulting in size and manufacturing cost reductions.

The feedthrough filter capacitor assembly of the present invention generally comprises an internally grounded feedthrough filter capacitor having first and second electrode plates. A first passageway is formed through the capacitor through which a terminal pin extends in conductive relation with the first set of electrode plates. The terminal pin also extends through a conductive ground plane and an insulator in non-conductive relation. The insulator includes a ground plate conductively coupled to the ground plane. Means are provided for conductively coupling the capacitor second set of electrode plates and the insulator ground plates.

Typically, the ground plane comprises a ferrule which is conductively coupled to a housing for an active implantable medical device (AIMD), such as a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device, or the housing for the AIMD itself.

The present invention, however, is not limited strictly to implantable medical devices. It also has broad application to military, space, external medical, telecommunications, and other applications. It will be obvious to those skilled in the art, that anytime that a hermetic seal is utilized to protect the internal electronic packaging, that the invention described herein provides significant advantages.

The insulator ground plate set typically extends to a conductive outer peripheral surface of the insulator, which is conductively coupled to the ground plane. In a particularly preferred embodiment, the insulator ground plate comprises a set of ground plates.

The coupling means, in a particularly preferred embodiment, includes a conductive material at least partially extending into a second passageway of the capacitor in conductive relation with the second set of electrode plates. The conductive material also at least partially extends through a second passageway of the insulator so as to be in conductive relation with the ground plates. Thus, any EMI is transferred from the conductive terminal pin to the first set of electrode plates, to the second set of electrode plates, and to the set of ground plates of the insulator (such as by the conductive material, and then to the ferrule and housing of the active implantable medical device. The conductive material may comprise one or more ground pins, a ground wire, a solder material, a conductive thermosetting material, a weld, a braze, a conductive glass, or a conductive spring coil such as that shown and described in U.S. patent application Ser. No. 10/907,361, filed Mar. 30, 2005.

Preferably, the outer peripheral surface of the capacitor is non-conductive and no conductive electrical/mechanical connection is made between it or the ferrule or active implantable medical device housing or the like.

The ground plates which are integral to the insulator structure of the hermetic terminal can be constructed of a number of materials. For example, if the insulator is alumina ceramic, the embedded ground electrode plates can be of the group of silver, palladium silver, platinum, platinum alloys and many other materials that are common in the art. Multi-layer alumina substrates, for example, are very common in circuit board or substrate manufacturing. It is also a novel feature of the present invention that said electrode plates could be made of ferro-magnetic materials. For example, the ground electrode plates could be made of nickel. This has desirable advantages to provide not just a convenient means of providing a grounded pin to the feedthrough capacitor, but also importantly provides magnetic shielding for the device. This could be particularly important in an MRI environment where it is necessary to prevent saturation of a ferrite inductor in the presence of a main static magnetic field of a magnetic resonance imaging machine.

The assembly of the present invention may also include an inductor, such as a ferrite inductor slab, through which the terminal pin extends in non-conductive relation. Preferably, the inductor is disposed adjacent to the capacitor. The inductor may be disposed between the capacitor and the insulator. The capacitor and insulator are preferably disposed in relation to each other, such as being adjacent to each other, but separated by a non-conductive material. In this regard, the disclosure of U.S. patent application Ser. No. 10/825,900 filed Apr. 15, 2004 is incorporated by reference herein.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings:

FIG. 1 is a perspective view of an internally grounded quadpolar feedthrough filter capacitor embodying the present invention;

FIG. 2 is a cross-sectional view taken generally along line 2—2 of FIG. 1, illustrating a conductive ground pin conductively coupling ground electrode plates of a capacitor and ground plates of an insulator, in accordance with the present invention.

FIG. 5 is a cross-sectional view taken generally along line 5—5 of FIG. 2, illustrating an active electrode plate of the capacitor;

FIG. 6 is a cross-sectional view taken generally along line 6—6 of FIG. 2, illustrating a ground electrode plate of the capacitor;

FIG. 7 is an electrical schematic representation illustrating the filtering characteristics of the assembly of FIG. 1;

DETAILED DESCRIPTION OF THE PREFERRED EMBODIMENTS

Figure 8:
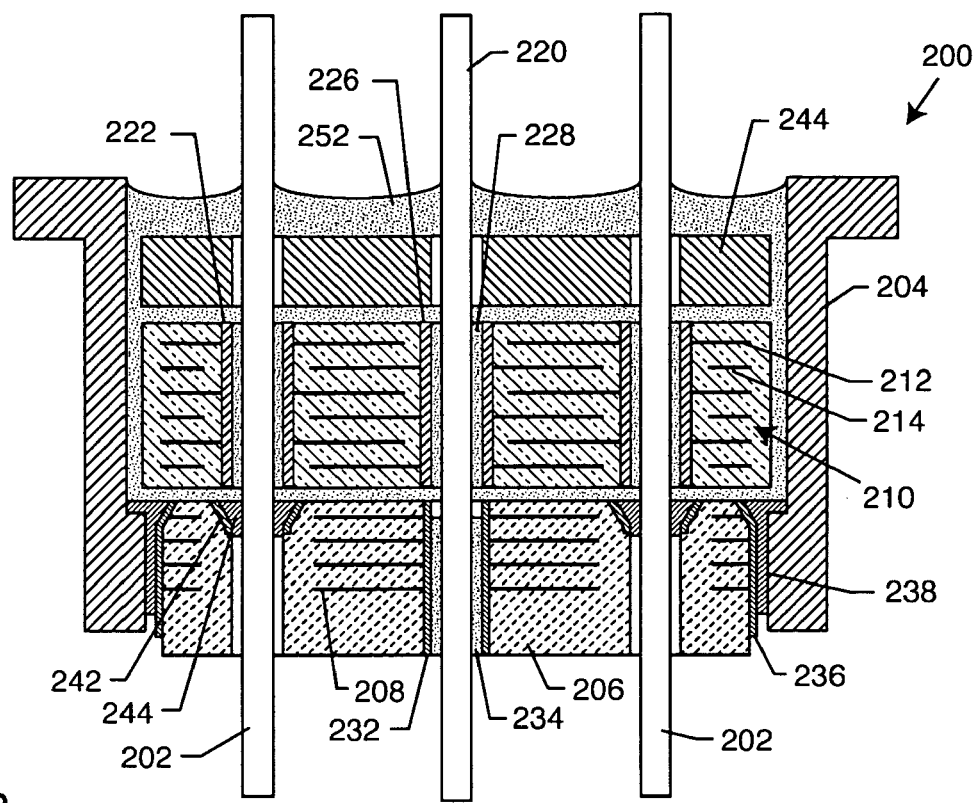
FIG. 8 is a cross-sectional view of a multi-polar capacitor feedthrough assembly incorporating the teachings of the present invention.
Figure 9:
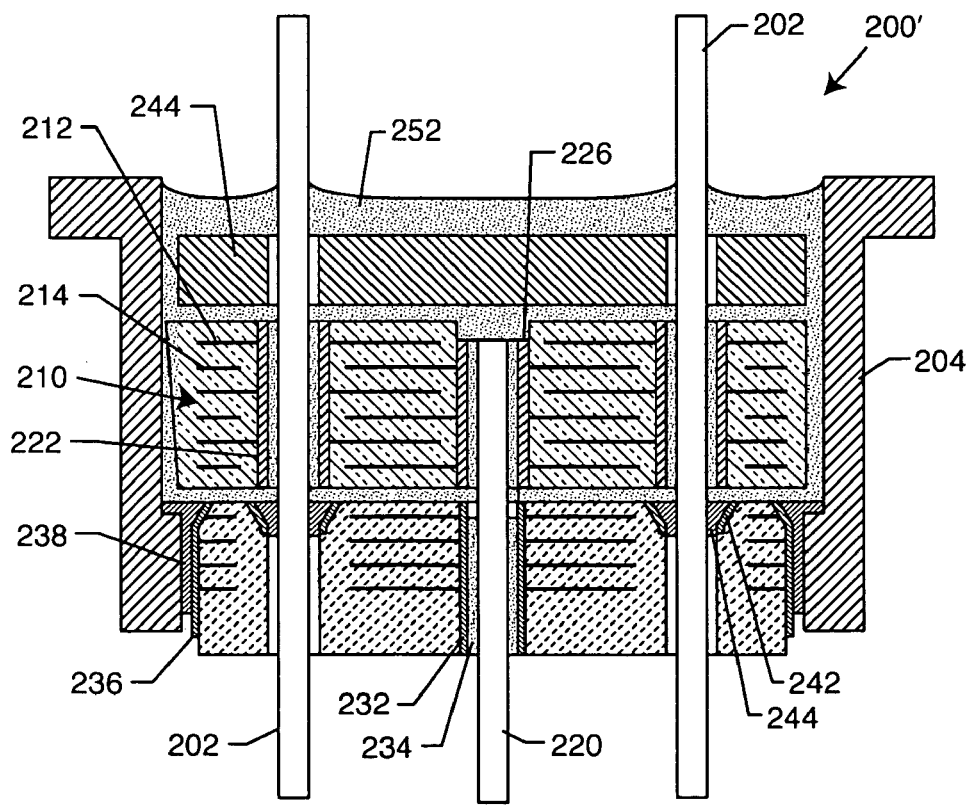
FIG. 9 is a cross-sectional view similar to FIG. 8, with a ground pin thereof only partially extending into a capacitor of the assembly.
Figure 10:
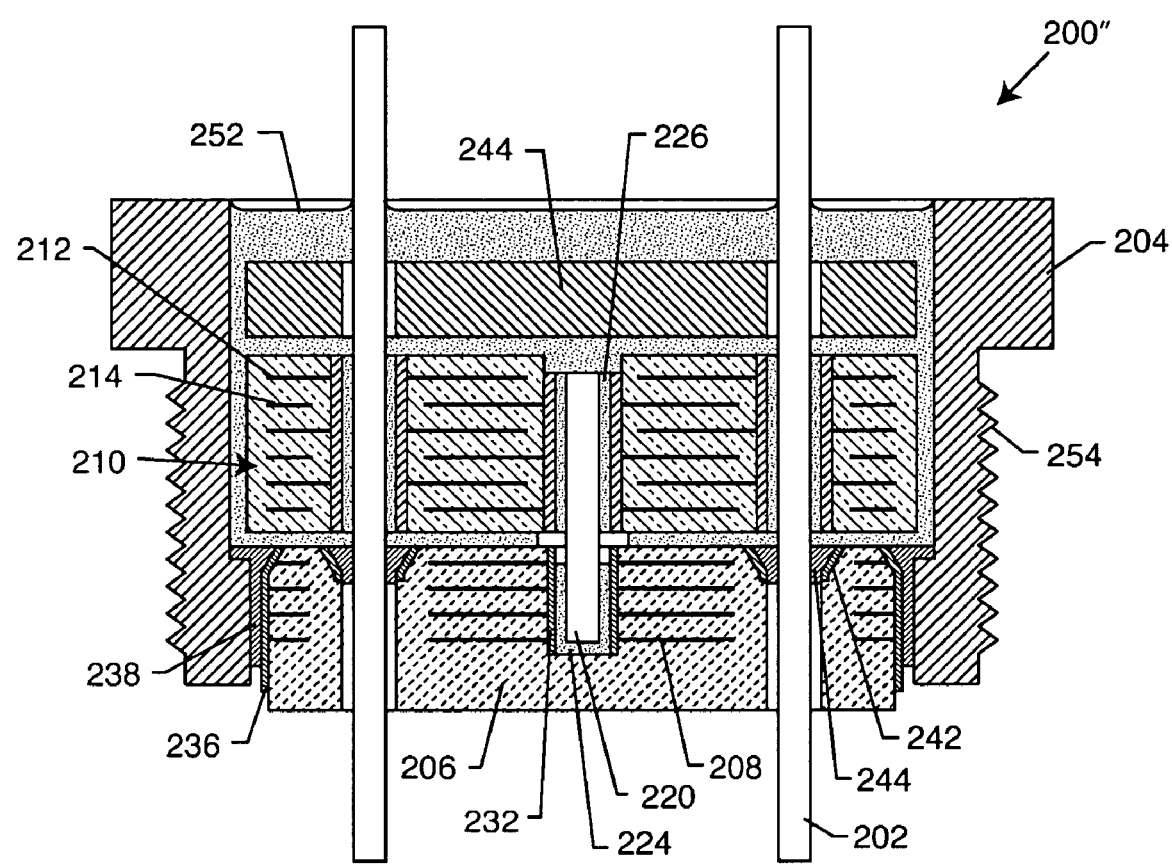
FIG. 10 is a cross-sectional view of another feedthough filter capacitor assembly, illustrating a ground pin thereof partially extending both into the capacitor and insulator so as to conductively couple ground plates thereof.
Figures 11, 12:
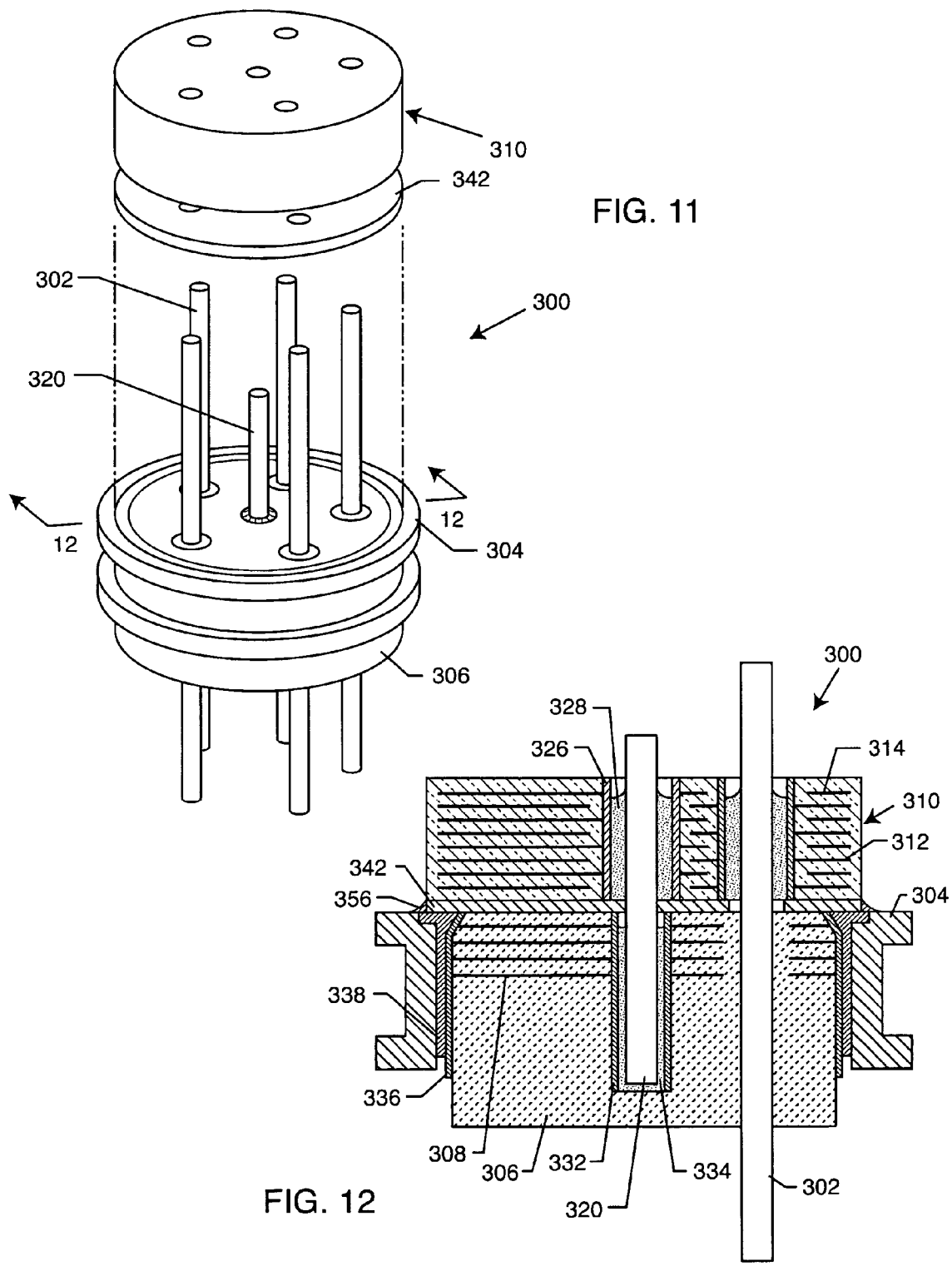
FIG. 11 is a partially exploded perspective view of a pentapolar feedthrough capacitor assembly embodying aspects of the present invention.
FIG. 12 is a cross-sectional view taken generally along line 12—12 of FIG. 11.
Figure 13:
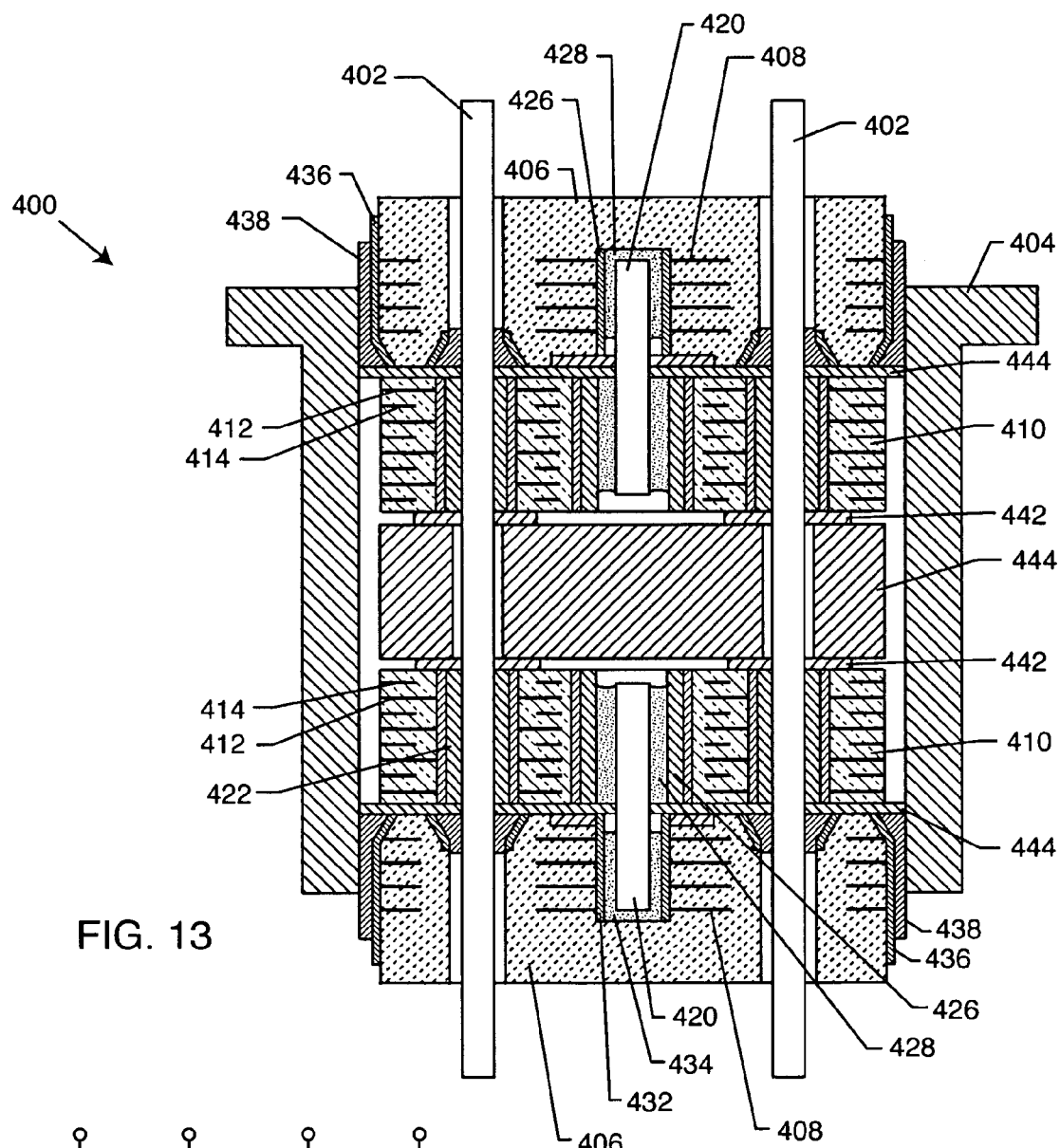
FIG. 13 is a cross-sectional view of a soldered-in quadpolar internally grounded PI filter EMI filter assembly embodying aspects of the present invention.
Figure 14:
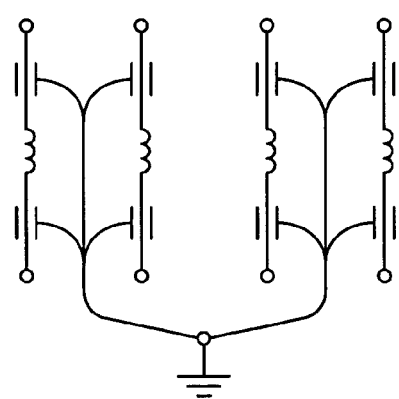
FIG. 14 is an electrical schematic representation for the assembly of FIG. 13.
Figure 15:
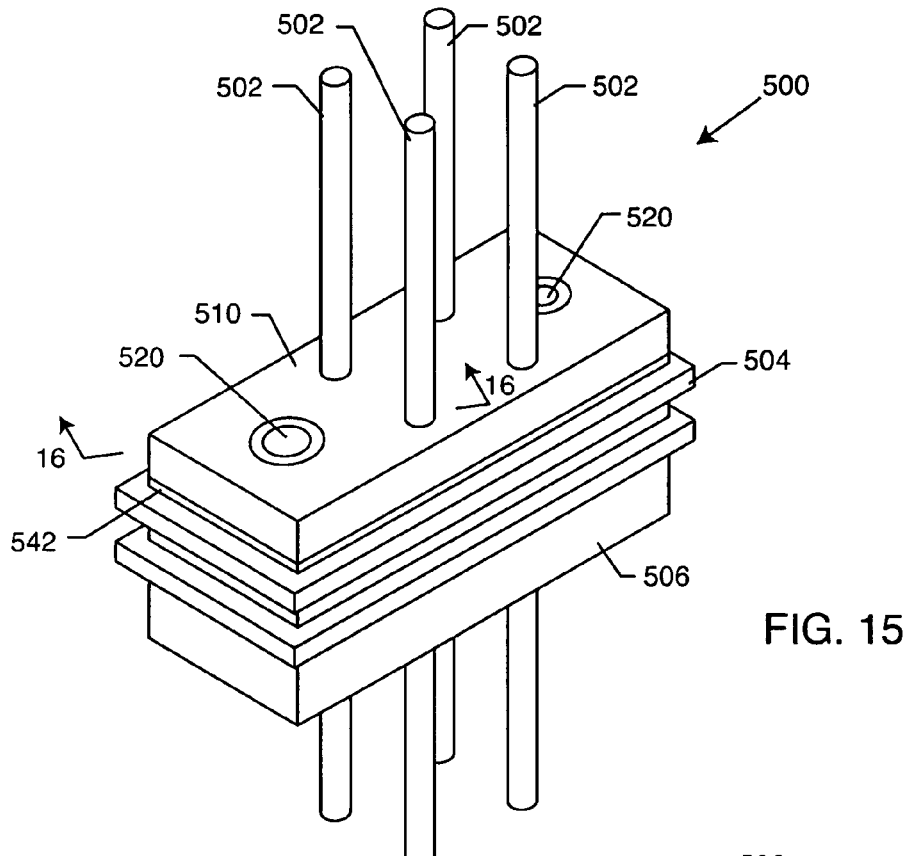
FIG. 15 is a perspective view of a rectangular internally grounded quadpolar feedthrough filter capacitor assembly embodying aspects of the present invention, and including two conductive ground pins.
Figure 16:
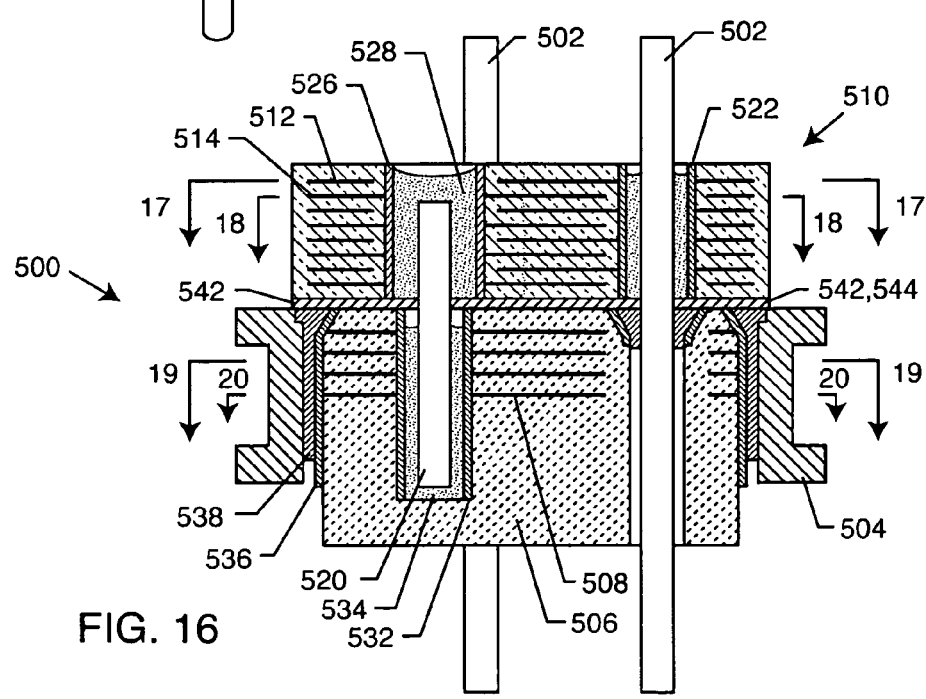
FIG. 16 is a cross-sectional view taken generally along line 16—16 of FIG. 15, illustrating internal components of the assembly.

As shown in the drawings, for purposes of illustration, the present invention is concerned with novel internally grounded feedthrough filter capacitor assemblies, generally designated in FIGS. 1–7 by the reference number 100, in FIGS. 8–10 by the reference 200, in FIGS. 11–12 by the reference number 300, in FIGS. 13–14 by the reference number 400, and in FIG. 17–21 by the reference number 500. In the following description, functionally equivalent elements of the various embodiments share the same reference number in increments of 100.

Referring initially to FIGS. 1–7, the improved feedthrough filter capacitor assembly 100 comprises, generally, a plurality (in this case four) conductive terminal pins (102) which extend through a conductive ferrule 104, in non-conductive relation, as will be more fully described herein. An insulator 106 (FIGS. 2 and 4) supports each conductive terminal pin relative to the conductive ferrule 104 in electrically insulated relation. The insulator 106 is typically comprised of an alumina ceramic material, although it is not limited to such. However, the insulator 106 must be comprised of an electrically non-conductive material. The alumina insulator 106 includes at least one embedded monolithic ground plate 108 (see FIG. 3), and preferably a plurality of ground plates 108 spaced apart from one another to form a set, whose purpose will be described more fully herein.

The feedthrough filter capacitor assembly 100 further includes an internally grounded feedthrough filter capacitor 110 that has first and second sets of electrode plates 112 and 114 (FIGS. 2, 5 and 6). Passageways 116 are provided through the feedthrough filter capacitor 110 through which the terminal pins 102 extend in conductive relation with the first set of electrode plates 112. The feedthrough filter capacitor 110 further includes a second passageway 118 into which a conductive ground pin 120 extends in conductive relation to the second set of electrode plates 114.

In accordance with the present invention, the feedthrough filter capacitor 110 includes a monolithic, ceramic, internally grounded feedthrough filter capacitor having two or more (in this instance five) passageways extending therethrough. The outer four passageways are configured to receive therethrough the respective conductive terminal pins 102, and the internal diameter of the first passageways 116 are metallized (at 122) to form a conductive link between the first set of electrode plates 112 and the conductive terminal pins 102. A conductive polyimide fill, solder, or the like 124 is placed within the first passageways 116 between the metallization 122 and the respective terminal pin 102 to electrically link the terminal pin with the respective first set of electrode plates 112. As is well understood in the art, both sets of electrode plates 112, 114 are typically silk-screened onto ceramic plates, forming the feedthrough filter capacitor 110. These plates 112, 114 are surrounded by an insulative ceramic material that, for purposes of the present invention, need not be metallized on its exterior surfaces, as will be more fully discussed herein.

Similarly, the inner diameter of the central or second passageway 118 through the feedthrough filter capacitor 110 is also metallized (at 126) to conductively connect the second set of electrode plates 114, also referred to as the ground plates of the feedthrough filter capacitor 110. As discussed above, the second passageway 118 is configured to receive therethrough the conductive ground pin 120. Again, a conductive polyimide, solder or other conductive fill 128 is placed within the second passageway 118 between the ground pin 120 and the metallization 126 to conductively couple the ground pin 120 to the second set of electrode plates 114.

In typical applications in the prior art, the second set of ground electrodes 114 extend to the outer periphery of the capacitor 110. The outer surface of the capacitor 110 is then metalized by metallization firing or plating operations, or otherwise providing external conductive connections between capacitor 110 and a ground, typically the conductive ferrule 104. However, as discussed previously, in addition to requiring extra manufacturing steps, forming such conductive connections places a great deal of stress on the capacitor 110 during the manufacturing process and also presents drawbacks of the joining of materials which are not perfectly matched in thermal coefficient of expansion.

The present invention, as described herein, eliminates the need for such external conductive connections between the capacitor 110 and the ferrule 104, or other ground. Typically, the conductive ferrule 104 is conductively mounted to a conductive substrate that may comprise, for example, the housing for an active implantable medical device. The ground pin 120, which is electrically and conductively coupled to the second set of electrode plates 114, as discussed above, extends into the insulator 106 so as to be conductively coupled with the one or more ground plates 108 of the insulator 106. More particularly, as illustrated in FIG. 2, the insulator 106 includes a passageway 130 adapted to receive the ground pin 120 therethrough. The ground plates 108 extend to the surface of this passageway 130, which is metallized (at 132) to conductively couple the ground plate 108 to one another. A conductive polyimide, solder, or other conductive fill 134 is placed within the passageway 130 to conductively couple the ground pin 120 to the ground plates 108.

Figure 3:
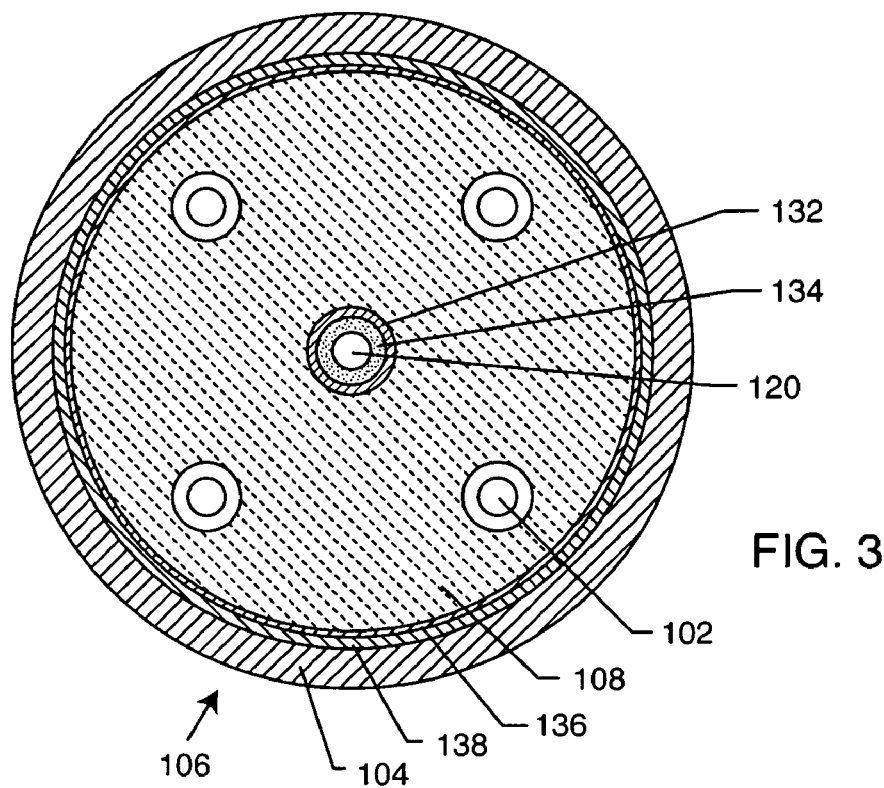
FIG. 3 is a cross-sectional view taken generally along line 3—3 of FIG. 2, illustrating a ground plate of the insulator.
Figure 4:
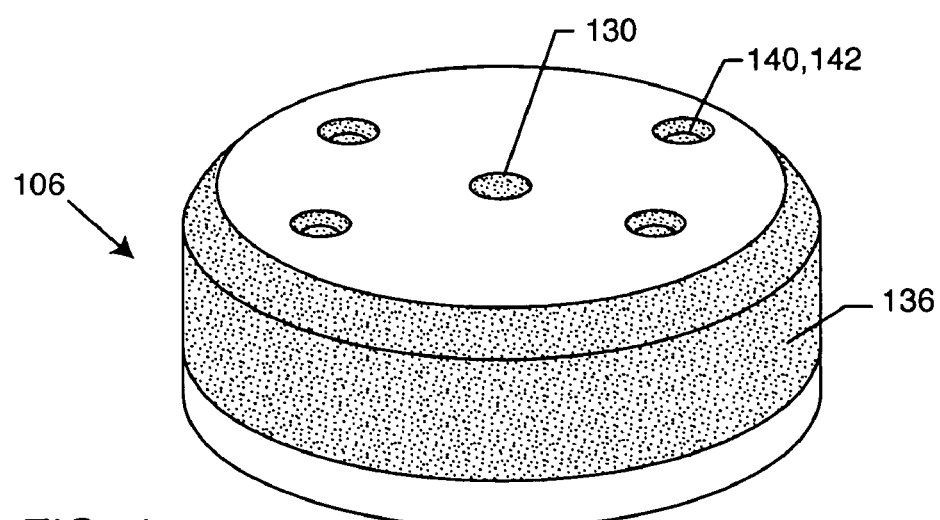
FIG. 4 is a side perspective view of the insulator of FIG. 2.

The ground plates 108, as shown in FIGS. 2 and 3, extend to the outer peripheral surface of the insulator 106, which includes a metallization 136 (FIG. 4). This metallization 136 can be formed by any means, including electroplating, thick film deposition, sputtering, or the like. The metallization 136 is conductively coupled to the ferrule 104, such as through the use of a conductive pre-form, solder, weld, or the like 138. Thus, the second sets of electrode plates 114 of the feedthrough capacitor 110 are conductively coupled through the internal ground pin 120, which in turn is conductively coupled to the one or more ground plates 108 of the insulator 106, which are conductively coupled to the ferrule 104.

Passageways 140 are also formed through the insulator 106, in general alignment with the capacitor passageways 116, for passage of the first conductive pins 102 therethrough. Due to the non-conductive nature of the material comprising insulator 106, the pins 102 could pass through in a frictional fit manner. However, in a particularly preferred embodiment, an upper beveled portion of the passageway 140 is metallized (at 142) such that a metal pre-form, such as gold or the like, or solder 144 can securely and hermetically connect the terminal pin 102 to the insulator 106. However, the metallization 142 does not come into contact with the one or more ground plates 108. Thus, the conductive pins 102 are electrically isolated from the ground plates 108 and the ferrule 104.

With continuing reference to FIG. 2, the capacitor 110 and insulator 106 are typically disposed relatively adjacent to one another and separated by a non-conductive material such as the illustrated washer 142. The washer 142 provides an insulative barrier between the isolated feedthrough filter capacitor 110 and the mounting surface of the insulator 106. The washer barrier 142 provides additional electrical isolation between the terminal pin 102 and ground pins 120, and provides mechanical stability for environmental exposure such as vibration and mechanical shock. The insulating washer 142 may be constructed by punching, laser cutting, or pre-forming a non-conductive polyimide matrix to the proper shape and number of feedthrough holes used in a material such as Abel Bond 71-7. The insulating washer 142 may also be constructed of a non-conductive epoxy which has been formed into a B-staged pre-form.

An optional inductor 144 may be associated with the capacitor 110, such as disposing the inductor 144 in between the capacitor 110 and the insulator 106, as illustrated in FIG. 2. An insulative washer 146, as described above, is disposed between the inductor 144 and the capacitor 110 to provide a physical separation between them. Passageways 148 are formed in the inductor 144, as necessary, such that the conductive pins 102 and 120 pass therethrough. It will be understood by those skilled in the art that the assembly 100 may incorporate one or more ferrite inductors 144 in various EMI filter circuit configurations as needed or desired. The electrical schematic for the configuration of the assembly 100 in FIGS. 1 and 2 is illustrated in FIG. 7.

As shown in FIGS. 1 and 2, the ground pin 120 may extend well above the capacitor 110 surface if needed for convenient connection of an internal circuit or substrate to the ground (ferrule 104 or medical implant device housing). However, the ground pin 120 does not have to penetrate all the way through the insulator 106.

With reference now to FIG. 8, the ground pin 220 may alternatively also extend through the insulator 206 to the body fluid side for convenient attachment to an electrode lead or the like. FIG. 8 illustrates a quadpolar internally grounded EMI filter capacitor 210 which is placed inside of a cylindrical cavity of a ferrule 204. The assembly 200 may be installed so as to protrude from or into a titanium housing of an active implantable medical device. An optional insulative polymer fill 252 may be provided over the capacitor 210, and inductor 244 if present, when installed within the ferrule 204.

As described above, the ground pin 220 is in conductive relation with the second set of ground plates 214, such as by use of a conductive polyimide, solder or other conductive fill 228 disposed between the ground pin 220 and the inner-metallization 226 of the passageway through the capacitor 210. The conductive pins 202 are in conductive relation with the first set of electrode plates 212, such as by contact with metallization 222 of the passageway. However, the terminal pins 202 are electrically isolated from the ground plates 208 of the insulator 206, such as by the gold braze pre-form metallization 242 and gold braze connection 244. The ground pin 220, however, is conductively coupled with the ground plates 208 by either direct contact thereto or more typically via a conductive fill or solder 234 and an inner-metallization 232 which conductively couples the plates 208. Similar to that described above, the plates 208 extend to an outer surface metallization 236, which is conductively coupled to the ferrule 204 or other ground plane, such as by the conductive connection 238, which may comprise a pre-form. The outer surface metallization 236 of the insulator 206 can be formed by many techniques, including metal deposition techniques, including flame spray, electric arc, chemical plating and electro plating techniques, as well as silk screening and firing on a conductive glass frit matrix, conductive electrode ink or other metallic thick film.

With reference now to FIG. 9, another assembly 200' is shown, similar to the assembly 200 of FIG. 8, but illustrating the ground pin 220 not penetrating all the way through the feedthrough filter capacitor 210. In this case, the exposed upper portion of the pin 220, and capacitor passageway is sealed with a non-conductive epoxy or polyimide 252. Thus, in this case, the ground pin 220 does not extend into the device, but rather only towards the body fluid side of the assembly 200'.

With reference now to FIG. 10, if the ground pin 220 need not extend beyond the capacitor 210 surface nor the insulator 206 surface, it can extend only partially or even fully through the capacitor 210 and insulator 206, without being accessible for connection on either end, as illustrated in FIG. 10. The ground pin 220 still serves the purpose of internally grounding the capacitor 210, as it is conductively coupled to the second set of ground electrode plates 214 and the ground plates 208 of the insulator 220, which are conductively coupled to the ferrule 204. In this assembly 200'', the ferrule 204 includes external threads 254 for convenient screw-in installation into a threaded hole or into a bulk-head with a nut and lock washer of the medical device housing or the like. Optionally, a knurled surface (not shown) can be used for installation by pressing into a mating hole into the bulk head or plate. These configurations may be applicable to any of the ferrules illustrated if deemed necessary or desirable. Once again, the capacitor 210 "floats" within the ferrule 204 cavity in insulative relation to the alumina insulator 206, protecting it from damage during assembly or installation.

Referring once again to FIG. 10, it is not necessary that the pin shown as 220 be a separate conductive lead wire. That is, pin 220 could be eliminated and instead the entire area could be filled with a thermal-setting conductive adhesive, a conductive polyimide, or the like, which is shown as material 224. In other words, material 224 could simply fill the entire via hole between capacitor 210 and the internally grounded insulator 206. Alternative materials also include the group of solders, conductive paste, brazes and welds.

With reference now to FIGS. 11 and 12, yet another assembly 300 embodying the present invention is shown. The assembly 300 comprises a pentapolar feedthrough filter assembly having an internal ground pin 320 conductively coupling the second set of capacitor electrode plates 314 to the ground plates 308 of the insulator 306 for grounding to the ferrule 304. It will further be appreciated, as with the embodiments illustrated and described above, that the electrode patterns of both the first and second sets of electrode plates 312 and 314 do not extend to the outer diameter of the feedthrough capacitor 310. This allows the outside surface of the feedthrough capacitor 310 to be non-conductive or insulative. In this embodiment 300, the feedthrough capacitor 310 is fitted outside of the ferrule 304, in this case, the capacitor 310 is separated by insulative barrier washer 342 from the alumina insulator 306. The insulator 342 may be double-sided adhesive to adhere the capacitor 310 and insulator 306 to one another. A hermetic seal 356 may additionally be formed with braze, solder, adhesive or any other suitable material. As will be appreciated by those skilled in the art, the ground pin 320 is preferably generally centered with respect to the conductive terminal pins 302, although, the invention is not limited to such a configuration.

With reference now to FIGS. 13 and 14, a PI (π) circuit EMI feedthrough filter capacitor assembly 400 is illustrated. Here, two ground pins 420 are utilized with their respective pair of feedthrough capacitors 410 and insulators 406 containing ground plates 408, as illustrated and described above. The pair of feedthrough capacitors 410 and insulators 406 are disposed on opposite sides of an intermediate inductor 444. The inductor 444, capacitors 410, and insulators 406 are separated by insulative washers 442 and 444. The electrical schematic for the assembly 400 is illustrated in FIG. 14.

Figure 17:
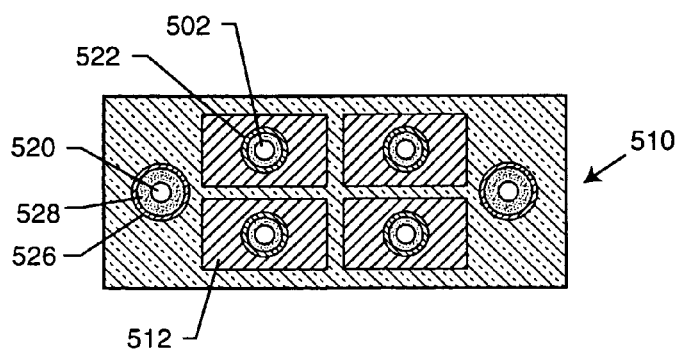
FIG. 17 is a cross-sectional view taken generally along line 17—17 of FIG. 16, illustrating active electrode plates of the capacitor of the assembly.
Figure 18:
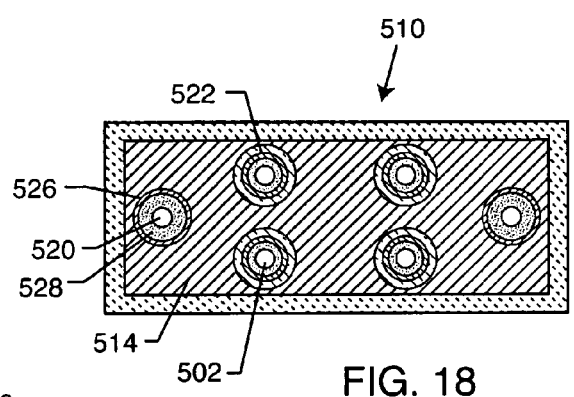
FIG. 18 is a cross-sectional view taken generally along line 18—18 of FIG. 16, illustrating a ground electrode plate of the capacitor.
Figure 19:
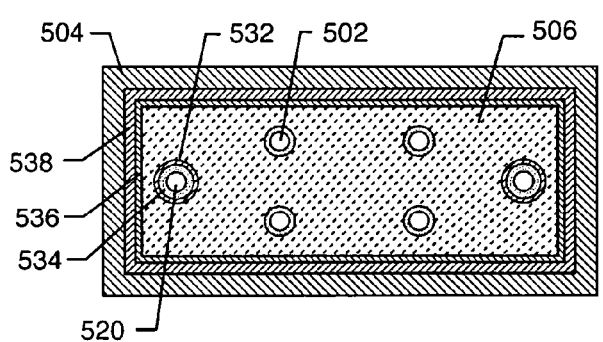
FIG. 19 is a cross-sectional view taken generally along line 19—19 of FIG. 16, illustrating passage of the terminal pins through the insulator, in accordance with the present invention.
Figure 20:
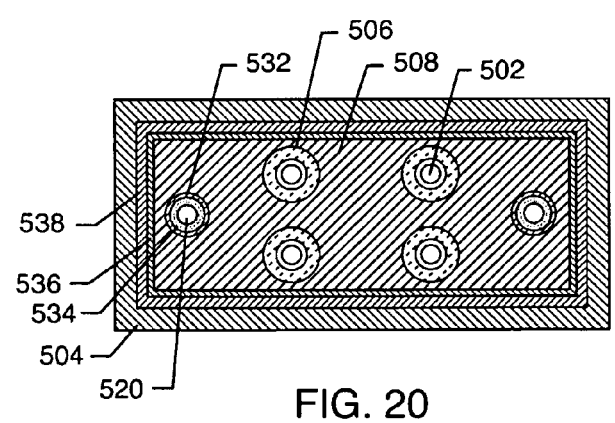
FIG. 20 is a cross-sectional view taken generally along line 20—20 of FIG. 16, illustrating conductive coupling of two ground pins with a ground plate of the insulator, in accordance with the present invention.

FIGS. 15–20 illustrate a quadpolar feedthrough filter capacitor assembly 500 which utilizes a pair of ground pins 520 to conductively couple the second set of electrode plates 514 of the capacitor 510 with the ground plates 508 of the alumina insulator 506 for grounding to the ferrule 504, as described above. Terminal pins 502 (a total of four in this embodiment) are conductively coupled to the first set of electrode plates 512, but pass through the ferrule 504 and the alumina insulator 506 in non-conductive relation, as described above. Conductive coupling of the pins 502 and 520 with the first and second electrode plates 512 and 514 are illustrated in FIGS. 17–18. Similarly, conductive coupling and non-conductive coupling of the pins 502 and 520 with the ground plates 508 are illustrated in FIGS. 19 and 20.

The significant advantage of the novel internally grounded feedthrough capacitor assemblies, as described herein, is that the mechanical (and electrical) connection to the outer surface of the capacitor is eliminated. In addition to eliminating manufacturing operations and reducing costs, this has the added effect of greatly reducing the mechanical stresses coupled to the relatively brittle ceramic capacitor structure caused by the mismatch in the thermal coefficient of expansion of the ceramic capacitor and the terminal or substrate to which it is mounted. This is particularly important for medical implant devices where the combined filter capacitor and hermetic terminal see high terminal stresses due to the requirement to weld such structure to the housing of a medical implant device. Thus, the capacitor structure is allowed to "float" in relative isolation from the surrounding materials. By elimination of the mechanical and electrical connection to the outside perimeter or outside diameter, the possibility of an adjunct or false hermetic seal is reduced or eliminated. Another benefit is that the penetration of the internal electrode plates to the external perimeter or outside diameter of the capacitor has been eliminated. This results in a more physically robust capacitor design with less tendency to delaminate along the knit line for internal electrode lamination layer. Accordingly, there would be less tendency for the capacitor to fracture, delaminate or otherwise structurally fail under thermal, mechanical or piezoelectric stresses. The only point of capacitor electrode penetration is the inside diameter of the cylindrical passageways for terminal pin connection. This tends to make the feedthrough capacitor a more solid, monolithic structure which is more resistant to moisture or solvent penetration. As the brittle ceramic capacitor is isolated from the ferrule, the capacitor is much more resistant to damage during ferrule installation by soldering, pressing, or screw-in torque. The capacitor, being isolated from the case or ferrule, makes it much more resistant to gripping tools which are used by the customer during installation.

As previously mentioned, internally grounded feedthrough capacitors are known in the art and described by U.S. Pat. Nos. 5,905,627 and 6,529,103. These two patents describe internally grounded capacitors with various means for connecting the capacitor's second set (or ground electrode set) of electrodes to a terminal pin which is part of the ferrule. The significant advantage of the novel internally grounded hermetic insulator is that this eliminates the need for one or more conductive terminal pins to be brazed or welded into the ferrule itself. This is particularly important for cylindrical EMI filter hermetic terminal assemblies. The reason for this is it is quite difficult to extend a web plate across the ferrule to the center of the capacitor. It is far better to have an insulative structure between the capacitor or inductor and the alumina insulator structure 106. The present invention eliminates the need for a web plate and welded terminal pin which is, effectively, all part of the ferrule. The present invention also provides a high degree of volumetric efficiency in that by elimination of the web plate there is no need to increase the overall height of the EMI filter terminal assembly. Referring once again to FIG. 2, one can see that the addition of the internal ground electrode plates 108 into the hermetic insulator 106 does not substantially increase the overall height of the hermetic insulator at all. Accordingly, it is a primary feature of the present invention to provide a grounding pin or conductive material 120 for grounding the capacitor second electrode plate set in such a way that the overall volume of the assembly is not increased at all.

Although several embodiments of the invention have been described in detail for purposes of illustration, various modifications of each may be made without departing from the spirit and scope of the invention. Accordingly, the invention is not to be limited, except as by the appended claims.

What is claimed is:

1. A feedthrough filter capacitor assembly, comprising:
   a conductive terminal pin;
   a feedthrough filter capacitor having first and second sets of electrode plates, a first passageway through which the terminal pin extends in conductive relation with the first set of electrode plates;
   a conductive ground plane through which the terminal pin extends in non-conductive relation;
   an insulator having a first passageway through which the terminal pin extends in non-conductive relation, and a ground plate conductively coupled to the ground plane; and
   means for conductively coupling the capacitor second set of electrode plates and the insulator ground plate.

2. The assembly of claim 1, wherein the insulator ground plate comprises a set of ground plates.

3. The assembly of claim 2, wherein the coupling means includes a conductive material pin at least partially extending through a second passageway of the capacitor in conductive relation with the second set of electrode plates, and at least partially extending through a second passageway of the insulator in conductive relation with the set of ground plates.

4. The assembly of claim 3, wherein the conductive material comprises a ground pin, a ground wire, a solder material, a conductive thermal setting material, a weld, a braze, a conductive glass, or a conductive spring coil.

5. The assembly of claim 1, wherein the ground plane comprises a housing for an active implantable medical device.

6. The assembly of claim 5, wherein the active implantable medical device is a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

7. The assembly of claim 1, including an inductor through which the terminal pin extends in non-conductive relation.

8. The assembly of claim 7, wherein the inductor comprises a ferrite inductor slab.

9. The assembly of claim 7, wherein the inductor is disposed adjacent to the capacitor.

10. The assembly of claim 9, wherein the inductor is disposed between the capacitor and the insulator.

11. The assembly of claim 1, wherein an outer peripheral surface of the capacitor is non-conductive.

12. The assembly of claim 1, wherein the insulator comprises an alumina insulator.

13. The assembly of claim 1, wherein the insulator ground plate extends to a conductive outer peripheral surface of the insulator.

14. The assembly of claim 13, wherein the conductive outer peripheral surface of the insulator is conductively coupled to the ground plane.

15. The assembly of claim 1, wherein the capacitor and insulator are disposed adjacent to each other and separated by a non-conductive material.

16. A feedthrough filter capacitor assembly, comprising:
a conductive terminal pin;
a feedthrough filter capacitor having first and second sets of electrode plates, a first passageway through which the terminal pin extends in conductive relation with the first set of electrode plates;
a conductive ground plane through which the terminal pin extends in non-conductive relation;
an insulator having a first passageway through which the terminal pin extends in non-conductive relation, and a ground plate conductively coupled to the ground plane; and
a conductive material at least partially extending through a second passageway of the capacitor in conductive relation with the second set of electrode plates and at least partially extending through a second passageway of the insulator in conductive relation with the ground plate, for conductively coupling the capacitor second set of electrode plates and the ground plate.

17. The assembly of claim 16, wherein the conductive material comprises a ground pin, a ground wire, a solder material, a conductive thermal setting material, a weld, a braze, a conductive glass, or a conductive spring coil.

18. The assembly of claim 16, wherein the ground plane comprises a housing for an active implantable medical device.

19. The assembly of claim 18, wherein the active implantable medical device is a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

20. The assembly of claim 16, including an inductor through which the terminal pin extends in non-conductive relation.

21. The assembly of claim 20, wherein the inductor comprises a ferrite inductor slab.

22. The assembly of claim 20, wherein the inductor is disposed adjacent to the capacitor.

23. The assembly of claim 22, wherein the inductor is disposed between the capacitor and the insulator.

24. The assembly of claim 16, wherein an outer peripheral surface of the capacitor is non-conductive.

25. The assembly of claim 16, wherein the insulator comprises an alumina insulator.

26. The assembly of claim 16, wherein the insulator ground plate extends to a conductive outer peripheral surface of the insulator which is conductively coupled to the ground plane.

27. The assembly of claim 16, wherein the capacitor and insulator are disposed adjacent to each other and separated by a non-conductive material.

28. The assembly of claim 16, wherein the insulator ground plate comprises a set of ground plates.

29. A feedthrough filter capacitor assembly, comprising:
a conductive terminal pin;
a feedthrough filter capacitor having first and second sets of electrode plates, and a first passageway through which the terminal pin extends in conductive relation with the first set of electrode plates;
a conductive housing for an active implantable medical device and through which the terminal pin extends in non-conductive relation;
an insulator having a first passageway through which the terminal pin extends in non-conductive relation, and a ground plate extending to a conductive outer peripheral surface of the insulator that is conductively coupled to the housing; and
a conductive material at least partially extending through a second passageway of the capacitor in conductive relation with the second set of electrode plates, and at least partially extending through a second passageway of the insulator in conductive relation with the ground plate for conductively coupling the second set of electrode plates and the housing.

30. The assembly of claim 29, wherein the conductive material comprises a ground pin, a ground wire, a solder material, a conductive thermal setting material, a weld, a braze, a conductive glass, or a conductive spring coil.

31. The assembly of claim 29, wherein the active implantable medical device is a cardiac pacemaker, an implantable defibrillator, a congestive heart failure device, a hearing implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

32. The assembly of claim 29, including an inductor through which the terminal pin extends in non-conductive relation.

33. The assembly of claim 32, wherein the inductor comprises a ferrite inductor slab.

34. The assembly of claim 32, wherein the inductor is disposed adjacent to the capacitor.

35. The assembly of claim 34, wherein the inductor is disposed between the capacitor and the insulator.

36. The assembly of claim 29, wherein an outer peripheral surface of the capacitor is non-conductive.

37. The assembly of claim 29, wherein the insulator comprises an alumina insulator.

38. The assembly of claim 29, wherein the capacitor and insulator are disposed adjacent to each other and separated by a non-conductive material.

* * * * *